(12) United States Patent
Nordhoff et al.

(10) Patent No.: US 6,627,410 B2
(45) Date of Patent: Sep. 30, 2003

(54) PROCESSING PROTEINS FROM GELS FOR ANALYSIS USING MASS SPECTROMETRY

(75) Inventors: Eckhard Nordhoff, Berlin (DE); Helmut Meyer, Recklinghausen (DE); Martin Schurenberg, Tarmstedt (DE)

(73) Assignee: Bruker Daltonik GmbH, Bremen (DE)

( * ) Notice: Subject to any disclaimer, the term of this patent is extended or adjusted under 35 U.S.C. 154(b) by 0 days.

(21) Appl. No.: 09/829,402

(22) Filed: Apr. 9, 2001

(65) Prior Publication Data

US 2002/0045204 A1 Apr. 18, 2002

(30) Foreign Application Priority Data

Apr. 15, 2000 (DE) .......................... 100 18 788

(51) Int. Cl.[7] .............. C12Q 1/37; C12Q 1/00; G01N 33/53
(52) U.S. Cl. .............. 435/23; 435/4; 435/283.1; 435/288.3; 435/288.4; 250/288
(58) Field of Search .............. 435/23, 4, 283.1, 435/288.3, 288.4; 250/288

(56) References Cited

U.S. PATENT DOCUMENTS 5,808,300 A * 9/1998 Caprioli ............ 250/288
5,853,894 A * 12/1998 Brown ............ 428/422

FOREIGN PATENT DOCUMENTS

GB   2 236 185   3/1991

* cited by examiner

Primary Examiner—Louise N. Leary

(57) ABSTRACT

The invention relates to methods and devices used for digesting small amounts of protein in tiny cut gel pieces and for extracting the peptides resulting from the digestion in preparation for analysis by mass spectrometry.

The invention involves digesting proteins using enzymes within the gel pieces in vessels which have permeable but lyophobic bases in such a manner that they scarcely touch the walls of the vessel, and then rapidly removing the digested proteins from the gel pieces almost completely by gentle centrifuging. It is then advantageous to bond the peptides reversibly to suitable surfaces as quickly as possible. For this purpose, the bases of the vessels may contain structures for bonding the peptides which are suitable for washing and subsequently eluting the peptides. A number of vessels can be combined together to form plates which, for example, can have the size of microtiter plates.

18 Claims, 1 Drawing Sheet

PROCESSING PROTEINS FROM GELS FOR ANALYSIS USING MASS SPECTROMETRY

FIELD OF INVENTION

The invention relates to methods and devices used for digesting small amounts of protein in tiny cut gel pieces and for extracting the peptides resulting from the digestion in preparation for analysis by mass spectrometry.

The invention involves digesting proteins using enzymes within the gel pieces in vessels which have permeable but lyophobic bases in such a manner that they scarcely touch the walls of the vessel, and then rapidly removing the digested proteins from the gel pieces almost completely by gentle centrifuging. It is then advantageous to bond the peptides reversibly to suitable surfaces as quickly as possible. For this purpose, the bases of the vessels may contain structures for bonding the peptides which are suitable for washing and subsequently eluting the peptides. A number of vessels can be combined together to form plates which, for example, can have the size of microtiter plates.

PRIOR ART

Two-dimensional gel electrophoresis is still one of the best and most widely used methods for separating the proteins of a cell aggregate—the so-called "proteome". When used after enzymatic digestion of proteins to peptides, mass spectrometry is the most sensitive methods for identifying individual proteins and determining their structure. The method itself and the difficulties encountered in using it will be briefly described in the following.

After separation in the gel, the proteins are stained and small samples of the gel containing the protein of interest are cut or punched out around the stain site. The gel samples are placed in a vessel and the stain is removed. Topping up with an enzyme solution (such as trypsin) leads to selective digestion at the cleavage sites determined by the enzyme. When using trypsin, which cleaves the molecule at two specific amino acids, the digestion produces peptides with a broad molar mass distribution around an average of approx. 1000 atomic mass units. The protein is usually clearly characterized by the exact masses of the peptides produced by the digestion. The peptides are able to diffuse inside the gel and slowly migrate out of the gel into the surrounding liquid within a few hours.

The peptides in the fluid are purified and analyzed by a suitable method of analysis using mass spectroscopy. In this method, the molecules are usually ionized by so-called Matrix Assisted Laser Desorption Ionization (MALDI) and the precise masses of the peptides resulting from digestion are measured in a time-of-flight (TOF) mass spectrometer. Other methods of ionization are known and are used, usually with confirmation from other types of mass spectrometer. For the MALDI-TOF analysis, the peptides produced by digestion are introduced on suitable sample carriers into small crystals of matrix substances and bombarded with laser pulses in a mass spectrometer. Their precise masses are determined by the flight time of the ions in the TOF mass spectrometer.

Even if some of the peptides are lost during the processing stage, precisely measured values of the peptides which are still available usually result in clear identification of the protein when a suitable program is used to search the protein sequence databases. It is possible to clarify ambiguous identifications by extensive measurement of the fragments of individual peptides produced by using special methods and elucidating them via their internal structure. This form of identification means that the protein, if known, can be characterized by its name, code, origin and molecular structure.

Details on the measurement of fragmentation and other methods for de-novo sequencing of proteins will not be given here.

Although such a straightforward method for the identification of proteins has been the subject of interest for the past few years, interest is now increasingly being directed toward the differences found between the proteins examined and those in the database. These differences, which relate to the mutative or post-translational changes in the proteins, are and will be the focus of interest in the future. For this, it is not only necessary to be able to measure only a few peptides, which in most cases is sufficient for identification purposes alone, but all possible peptides produced by the digestion. In the methods briefly described above however, many peptides are lost due to their being adsorbed on the walls of the vessel which contains them.

At the same time, it is not only the very concentrated proteins which are present in the gel at concentrations ranging from 10 to 100 picomol which are of interest, but also those at lower concentrations ranging from 10 to 100 femtomol. Now if, for example, 20 femtomol of a peptide is present in 20 microliters of liquid, the individual molecules produced by the digestion process will diffuse freely throughout the liquid and will come into contact with the walls of the vessel many times over within a matter of hours. In a small vessel of around three millmeters diameter, they will come into contact with a wall surface area of around 40 $mm^2$. If the wall selectively adsorbs one of the peptides, then that peptide will cover the whole surface with a layer which is at least molecule deep. This monomolecular layer could adsorb approx. 40 picomol of a peptide of 1,000 atomic mass units, i.e. 2,000 times the amount which is available in the solution in our example. Even if the adsorptivity of the vessel wall could be reduced to one thousandth by taking the appropriate measures, the peptide of interest could still be fully adsorbed onto the surface and, if the adsorption bond is irreversible as is frequently the case, there is no way that the peptide could be brought into solution again.

The 20 microliter solution sample used in the example calculated here is currently regarded as large. Converting this sample size to a 1 microliter or 100 nanoliter sample (for the same concentration of test molecule) would increase the effect of coming into contact with the wall dramatically.

In modern biochemistry and molecular biology, samples are typically processed in large numbers simultaneously. A visible exponent of this development is the so-called microtiter plate consisting initially of 96, then 384 and now 1,536 reaction vessels. Recently, a NanoWell™ plate was introduced with 3,456 reaction vessels. Increasing the number still further and providing the tools for processing is only a question of time. Appropriate pipetting and processing robots with storage positions for many microtiter plates, barcode labeling, multi-pipette heads and multi-dispensing systems have been developed for microtiter plates which have been in common use until now.

At the same time, the quantities of sample molecules required for the chemical, enzymatic and analytical processing stage are getting increasingly smaller so that proteins at very low concentration can also be measured. Processing has long since moved from the nanomol range to the picomol, femtomol and even attomol range. The disadvantage of this is that, as the amounts of test solution are progressively reduced, the wall area of the cavities enclosing the liquid progressively increases in relation to their volume and the chemical and physical effects of the cavity walls on the reactions during processing become more critical.

The microtiter plate also forms the ideal basis for processing the proteins of a proteome, for example, in association with an automated gel sampler. Until now, however, microtiter plates have whisked away a large proportion of the peptides produced by the digestion.

OBJECTIVE OF THE INVENTION

The objective of the invention is to find methods and devices to be used for preparing small samples of protein from pieces of gel for analysis using mass spectrometry but which are characterized by high yields for all peptides and particularly low levels of peptide loss for those peptides which are at risk through wall adsorption.

SUMMARY OF THE INVENTION

In detail, the method of the invention uses tiny gel pieces containing protein and relates to the enzymatic digestion of proteins within the gel which involves the following steps:

1) The gel pieces containing the proteins are placed in vessels with lyophobic porous bases.
2) Enzyme solution is added to the gel pieces but only as much as can be absorbed by them.
3) The proteins in the gel pieces are digested.
4) The vessels with the gel pieces are centrifuged so that the enzyme solution containing the peptides produced by the digestion are forced out of the gel pieces and centrifuged out of the vessels.

It is particularly convenient if the peptides in the enzyme solution which has been forced out of the gel pieces are immediately and reversibly adsorbed onto peptide-adsorptive surfaces so that they are no longer available for uncontrolled wall adsorption.

In this case, a lyophobic surface is defined as a surface which is not only water repellent (i.e. not only hydrophobic) but is also repellent to the organic solvents used in peptide chemistry, such as methyl alcohol or acetonitrile at least in aqueous solutions over a wide concentration range.

The device according to the invention consisted of providing the vessel with a lyophobic porous base where the porosity of the base is achieved by using one or more lyophobic capillary channels. These can be closed off with fibrous membranes, close-packed particle structures, fritt-type structures or open-pore solid foams. A number of vessels, each with porous bases, can be combined together in a single plate the size, for example, of a microtiter plate. By specially preparing their surfaces to give them the necessary adsorption properties, these membranes, close-packed particle structures or solid foams can be used to bond to and immobilize the peptides. The capillary channels in the bases of the vessels are made lyophobic so that the repulsive effect of capillary action prevents the liquids which have been freshly placed in the vessels from flowing out of the vessels under normal gravitational force but allows them to escape under centrifugal force. The internal surfaces can also be made lyophobic so that liquids can rapidly coalesce on the surfaces and rapidly escape under the effect of centrifugal force. Apart from this, surfaces which have been made lyophobic cause the level of contact with the wall to diminish since liquids touching the wall will not spread and wet the surface.

Basically, according to the invention, the purpose of the method is to keep the molecular contact between the dissolved peptide and the wall, which is proportional to the product of the area of the wall in contact with the solution and the duration of contact, as low as possible. After the proteins have been digested, the peptides bond to suitable surfaces as rapidly and reversibly as possible so that they have to be kept away from any further, uncontrolled contact with the wall; this process is promoted by the device according to the invention. The required reversible bonding at suitable surfaces allows the peptides to be subjected to further processes, such as washing, and the reversibility of the bond allows the peptides to be measured using mass spectrometry, for example, by transferring them to suitable mass-spectrometric MALDI sample carriers.

It is particularly beneficial to free the gel pieces of a part of their internal liquid before or after filling the vessels in Step 1) of the method. Some of the internal liquid can be removed from the gels, for example, after depostion in the vessels by centrifuging, or better still, by partial vacuum drying. Vacuum drying gives the gel an open-pore structure, which is good for the absorption of the enzyme solution in Step 2), but the gels must not be allowed to dry completely as this will impair their ability to re-absorb the liquid.

The enzyme solution can be added in Step 2) by the method of pipetting, using multiheaded pipettes if necessary, or by contactless dispensing using Piezo or solenoid dispensers. The absorption of enzyme solution due to the swelling of the partially dried, porous gel pieces carries the enzymes rapidly and uniformly into the gel pieces which, because the enzymes must be able to migrate by diffusion, is not the case with gels which have not been partially dried. After the enzyme solution has been absorbed by the gel pieces, surface contact of the solution with the wall of the vessel is minimal. Since the diffusion of the peptides produced in Step 3) is widely limited within the gel pieces, losses due to wall adsorption are negligibly small.

The digestion in Step 3) of the method is accelerated by warming the vessel (incubation) to the digestion temperature and, at the optimum temperature, the digestion process is complete within two to four hours. Digestion is therefore the rate-determining step. During the incubation period, the vessels must be well sealed to prevent the gel pieces from drying out.

In Step 4), the centrifugal force drives the enzyme solution with the peptides produced by the digestion out of the gel pieces within a few seconds and they immediately may drop through the porous bases of the vessels into a set of collector vessels or onto mass-spectrometric sample carriers underneath. Very moderate centrifuging conditions at approx. 2,000 rpm are sufficient.

After or during this process, the peptides may bond to the surfaces either on the porous structures of the base of the vessel or on the particles which are in the collector vessel or on the sample carrier plates. The particles in the collector vessels may, for example, be tiny magnetic beads with suitably prepared surfaces; these can be held or moved back and forth in a predetermined manner through the washing liquids by magnetic forces. Areas on the surface of sample carriers can be coated with adsorptive layers such as $C_{18}$ alkyl chains to facilitate subsequent washing.

After the process has been completed in accordance with the invention, the peptides bonded to the surface can be washed in the usual manner and freed from enzymes, buffers, salts, and all remaining impurities. It is possible to release the peptides from the surface using an eluant solution such as 30% acetonitrile in de-ionized water and analyze the solution by mass spetrometrometry using, for example, sample carriers used for mass spectrometry.

It is also possible to place the peptides directly on MALDI sample-carrier plates during centrifuging without adsorptive bonding, for example, on plates prepared beforehand with MALDI matrix substances. In this method, it is better if alkaline metal salts are not used for the buffer solution. These can be substituted by ammonium carbonate.

PREFERRED EMBODIMENTS

Figure 1:
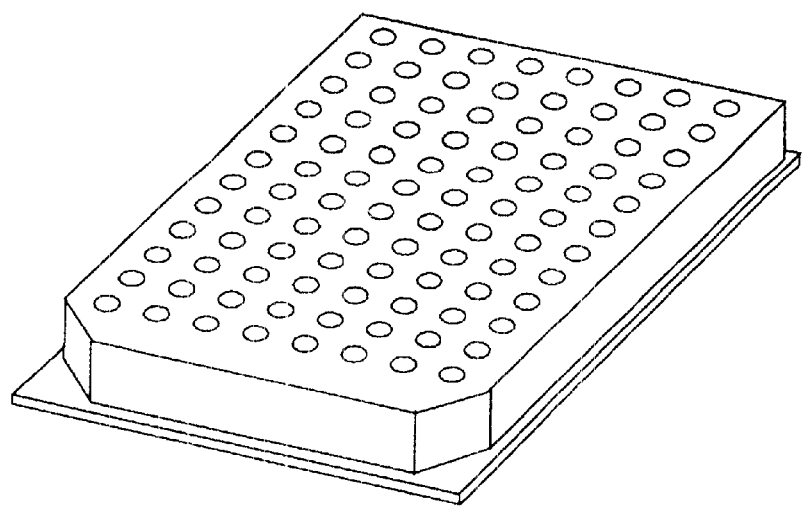
FIG. 1 shows a commonly used state-of-the-art microtiter plate, in this case, with 96 vessels. Versions with 384, 1536 and even more vessels are also available.
Figure 2:
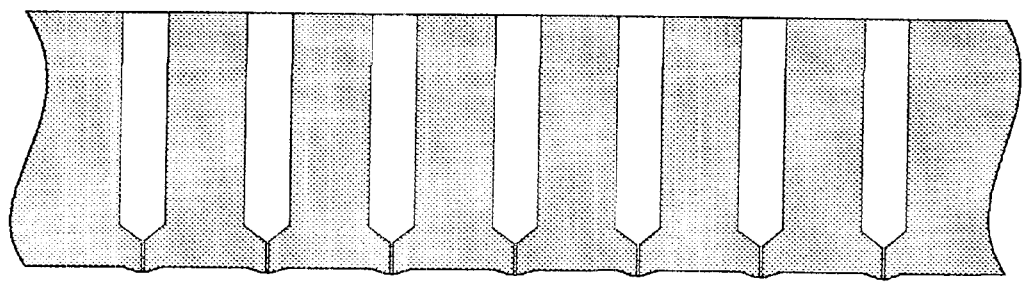
FIG. 2 shows a cross-section through a 384-vessel microtiter plate according to the invention, each vessel of which has a lyophobic capillary channel in the base. The channels do not contain chromatographic packing. The diameter is 1.8 mm and the channel diameter is 0.2 mm. The fluid contents are prevented from escaping by the repulsive capillary forces in the capillary channels. The capillary forces are only overcome by centrifuging and the liquid is ejected.

At first, two-dimensional gel electrophoresis is used as the separation procedure for proteins. Different methods based on one-dimensional gel separation can also be used, such as those which are applied using just the isoelectric point or the electrophoretic mobility.

A particularly favorable method uses a punch robot which automatically recognizes gel pieces which contain the protein by their color, punches them out of the moist gel and places them in the vessels with porous bases. Punch robots such as these are already commercially available in their initial form. They have cylindrical hollow punches with diameters ranging from 0.8 to 2 millimeters which punch out gel pieces which are round in shape. The hollow punches (fitted in place of pipettes on moveable heads) which push out the punched gel pieces, preferably using pipetting fluid or, less desirably, using gas, place them in the vessels. The punch robots contain cameras or scanners and recognition software for the dyed patches. Patches and proteins can be selected specifically for several gels either manually on the screen or automatically by using comparison programs.

For a small number of proteins, it is also possible to use hand punches with a high level of success. However, these require the original gel locations and their transfer to coded vessels to be well documented which, in both cases, is carried out automatically by punch robots.

The punches can be washed between punch cycles but, in practice, it has been found that proteins are almost never transferred from one gel piece to another.

The cavities in a microtiter plate designed according to the invention are suitable vessels. The microtiter plate can have 96, 384, 864 or even 1,536 cavities arranged in a 2.25, 3, 4.5 or 9 millimeter grid with the diameter of the cavities ranging between 1.5 and 2 millimeters. The bases of the cavities are fitted with lyophobic channels so that liquids are unable to escape under the normal force of gravity but can escape under the much higher centrifugal force of a centrifuge. The preferred diameter for the capillary channels is between 0.2 and 0.3 millimeter.

Microtiter plates are being developed with increasingly higher cavity densities as the original grid spacing of nine millimeters is divided by progressively higher integer numbers.

Pipetting fluid already suitable for ejecting the gel pieces is used preferredly to remove the color from the proteins if this will interfere with subsequent analysis mass spectrometry. After the gel pieces have been decolorized, they are centrifuged very carefully in order to avoid pressing them completely flat. The samples can then be subjected to one or several washing cycles, each of which includes pipetting, swelling and centrifuging. A multi-headed pipette with, for example, 96 or 384 pipettes is suitable for this and for subsequent pipetting steps so that all vessels can be filled in a few pipetting steps.

When the gel pieces have been washed sufficiently, they are partly freed of the internal liquid. This can be achieved initially by carefully centrifuging the gel pieces as they are in the washing procedures but the treatment is improved by subjecting the pieces to partial vacuum drying as well. Rapid, brief vacuum drying causes the source liquid to boil under reduced pressure and the vapor bubbles produce an open-pore structure in the gel which assists the absorption of the enzyme solution in the next step. The gel pieces must not be dried out completely as this will impair their ability to absorb liquid again.

The enzyme solution can be added in Step 2) of the procedure by pipette. The transfer of small amounts of enzyme solution requires the pipette droplets to come into contact with the gel. In practice, it has been found that almost no proteins are transferred from one gel piece to the next by the pipette tips. When using multi-head pipettes, this risk is reduced even further since only a small number of pipettings is required and only an insignificant amount of time may be lost in washing the pipettes between doses. The enzyme solution can also be added via contactless dispensing using piezo or solenoid dispensers in order to avoid transferring any trace of protein from one gel piece to another.

Absorption of the enzyme solution by capillary penetration and swelling of the partially dried and slightly porous gel pieces causes the enzyme to penetrate into them rapidly and uniformly. Gels which have not been partially dried do not have this advantage and have to rely on the diffusion rate of enzymes which is slow.

After the gel pieces have absorbed the enzyme solution, the contact areas available to the enzyme solution on the wall of the vessel are only minimal. Making the walls lyophobic reduces the contact areas still further since the liquid does not spread on the surface by wetting. Contact between the peptides which gradually appear is reduced because the contact surfaces are reduced in size and the diffusion within the gel pieces is significantly impaired. Losses due to wall adsorption are therefore negligibly small.

Digestion of the proteins at the cleavage sites determined by the enzyme is initiated and aided by warming the vessel to a suitable digestion temperature. Digestion using trypsin, for example, is complete in approx. two to four hours at the optimum temperature of 37° C. During the incubation period, the vessels must be well sealed to prevent the gel pieces from drying out. However, digestion by incubation is still the rate-determining step in the method according to the invention. Digestion within the gel is particularly effective because the proteins exist in a fully uncoiled state and therefore attack by the enzyme is not impeded by protective convolutions. Apart from this, it has been found from experience that the self-digestion of enzymes is also reduced in the gel.

After digestion, the enzyme fluid containing the peptides is driven out of the gel pieces by centrifugal force. This process only takes a few seconds. The liquid immediately passes through the porous bases into the collection vessels underneath. Centrifuging under very moderate conditions at approx. 2,000 rpm is sufficient to expel most of the liquid—ultracentrifuges are not necessary and are actually harmful.

In one embodiment, the enzyme solutions containing the peptides are placed directly on sample-carrier plates underneath which have been prepared beforehand with matrix substances for the mass spectrometric analysis. There, they are dried and are then ready for the analysis. Lyophilic anchors may also be present on the plates in a lyophobic environment to separate the solutions from different vessels from each other.

In another embodiment, the lyophilic anchors of the sample-carrier plates are coated with chemically covalent-bonded coatings with alkane chains, for example $C_{18}$, which adsorb the peptide reversibly. The peptides can then be washed and freed, in particular, from all alkali metal ions. Preparation can be completed for the mass spectrometric analysis by MALDI by adding a matrix substance dissolved in an aqueous acetonitrile solution and then drying.

Figure 3:
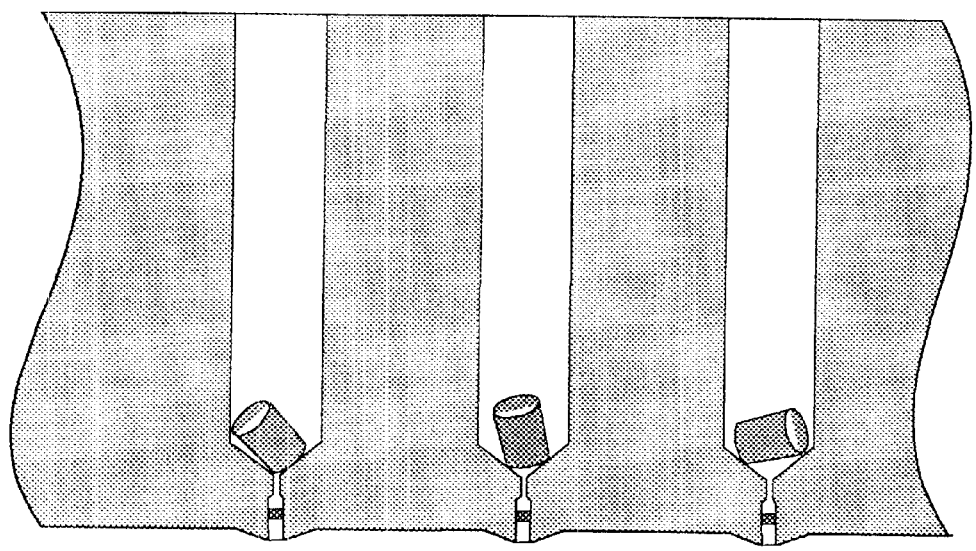
FIG. 3 shows an enlarged cross-section through a 384-vessel microtiter plate with gel pieces which have been punched out in the vessels, the lyophobic channels containing chromatographic packing in light extensions. The packing is an open-pore, solid foam with peptide-adsorptive properties which has been blown and polymerized in-situ so that it has a strong bond with the wall to withstand the centrifugal forces.

In another embodiment, the peptides are bonded to the surfaces of the porous structures of the vessel bases. The bases of the cavities must also be given special shape. The capillary holes are packed with chromatographic phases as shown in FIG. 3. Here, many of the phases used in liquid chromatography can be used, reverse phases for reverse-phase chromatography and affinity phases in particular. The coating should leave the upper, lyophobic openings of the capillary holes open so that the, in some cases, very hydrophilic phases do not immediately absorb the liquids from the cavities and cause them to escape. Extending the capillaries underneath makes it easier load the chromatographic phases.

The microtiter plates with porous, lyophobic channels can be made from plastic or metal. The capillary channels can already be made by the shape of the matrix when manufacturing microtiter plates but holes or laser holes can also be added later. In practice, it has been found that the gel pieces are not able to seal the channel exits from the vessels so that no fluid can escape, even in the case of vessels with smooth bases. However, it is beneficial to provide the vessel bases with narrow raised ribs or deepened grooves around the mouths of the capillaries to help the liquid to escape during centrifuging.

A lyophobic surface is understood here as a surface which is not only water repellent (i.e. not only hydrophobic) but is also repellent to most organic solvents such as methyl alcohol acetone or acetonitrile.

Recently, several methods for producing extremely lyophobic surfaces have become known which can be used for making the surfaces of the channels, vessel walls or even the whole microtiter plate lyophobic. The best known of these is to coat the surface with perfluorinated substances such as PTFE (for example, Teflon™). These coatings are both hydrophobic and oleophobic. While is was previously assumed that hydrophobicity and oleophobicity were mutually exclusive properties, this has been disproved by recent knowledge. Among other lyophobic agents are the novel organic/inorganic sol/gel nanocomposite materials (DE 41 18 184), see for example R. Kasemann, H Schmidt, S. Brück, Bol. Soc. Esp. Ceram. Vid. 31-6, Vol 7, (1992), 75. These nanocomposite materials can be baked onto metals, glass or plastics as scratch-free surfaces of only a few micrometers thick. PTFE coatings can also be made scratch-proof by adding ceramic components. The surfaces of molded parts made from suitable plastics such as polyethylene can be perfluorinated by a fluorine plasma produced by electrical discharge, which imparts lyophobic properties to them at the same time.

The coatings with the Lotus effect (W. Barthlott and C. Neinhuis, "Purity of the sacred lotus, or escape from contamination in biological surfaces", Planta 202 (1997), 1) belong only to a limited extent to this group of surfaces having both hydrophobic and oleophobic properties. They merely increase the repellent effect of surfaces which already have hydrophobic or lyophobic properties by a special sort of modification of the microstructure. According to the invention, this method of intensifying the lyophobic properties can also be applied to the vessels and channels.

Recently, special open-pore solid foams have become known for the bonding and cleaning of peptides, such as Poros™ in the form of tiny spheres or ZipTip™ in the form of chromatographic packing material in pipette tips. These open-pore solid foams consist of polymers which are introduced as monomeric solutions into the capillary bores where they can be expanded and polymerized (as shown in FIG. 3). They are especially suitable for the bonding and cleaning of peptides. These packings can be regenerated a few times over which means that the mictrotitration plates can also be reused to a limited extent.

Eluent solutions, such as 30% acetonitrile in water, can be used to scavenge the peptides and bring them into solution again but the peptide solution must then be subjected to mass-spectrometric analysis immediately afterwards in order to avoid losses due to wall adsorption.

In another embodiment of the invention, the underside of the microtiter plate is coated with a fibrous membrane which is pressed firmly by a counter plate with wide, lengthened channels. In this case, the channel exits are provided with a porous seal by the membrane. The membranes can be made adsorptive to peptides in a known manner and are easily replaced, so the microtiter plates can be reused any number of times. The peptides must adsorb on the surfaces of the membranes and not in the channels of the microtiter plates.

In another version of the method according to the invention, the peptides do not bond to the particle surfaces until they are in the centrifuging collection vessels. The preferred form of these particles in the collection vessels is as tiny magnetic beads prepared with adsorptive surfaces in a highly concentrated suspension. After the enzyme solutions with the peptides have been added by means of centrifuging, the tiny spheres can be distributed in the solution by ultrasonic treatment or alternating magnetic fields in so-called "magnetic rockers" or they can be repeatedly moved through the solution in order to bond all the peptides. Cleaning the peptides on the tiny magnetic spheres and then transferring them to MALDI plates is a procedure which is already known.

The microtiter plates with the vessels according to the invention are suitably provided with individual labels which can be read automatically in order to prevent confusion. This system allows the samples and the processes that they have gone through in the processing robots to be followed and recorded extremely accurately. The labels can be, for example, barcodes which are printed on to the surface or even integrated transponders which can be read by the processing robots.

The method according to the invention is an important step in the analysis of a proteome. Proteome means the totality of proteins in a cell aggregate. The method used to analyze a proteome is carried out as follows:

First of all, the proteins of a cell aggregate are separated using 2D gel electrophoresis and stained with a staining agent. Very good electrophoretic methods separate around 5,000 visible proteins and satisfactory methods yield approx. 2,000 proteins. A staining agent is selected which does not interfere with subsequent analyses or which can be removed later on. In pipette robots, tiny round gel pieces of around one millimeter in diameter are punched out. Punching them out and placing them in a vessel in a 384 microtiter plate takes around six seconds, which means that four 384 plates are charged with 1,536 gel pieces in about 2.5 hours. In less than eight hours, approx. 4600 proteins can be punched out in three cycles and at least a proportion of these will have undergone further treatment.

The moist gel pieces are automatically placed in the vessels in the microtiter plate according to the invention by the punch robot where they float in the liquid used to eject them from the punches. The liquid may, for example, be a de-colorising fluid for the proteins. The liquid protects the gel pieces from drying out during the lengthy punching process.

As described above, the method according to the invention which is used to digest the proteins to produce the peptides, centrifuging and bonding of the peptides to the surfaces, now takes place as described in detail above. Next, the peptides are usually washed in their immobilized state. Four 384 microtiter plates can be suitably treated in parallel. The cycle for incubation, centrifuging, washing, adsorption and transference to MALDI sample carriers is approximately equal to the time taken to punch out the proteins for the next four microtiter plates.

For the following description, it is assumed that a MALDI-TOF analysis is being carried out. The specialist will be familiar with the appropriate steps for further sample preparation for other types of analysis using mass spectrometry.

The peptides are desorbed using a solution of α-cyano-4-hydroxycinnamic acid in 30% acetonitrile and water. The solution which contains the peptides is immediately transferred to the MALDI carrier plates and dried. The MALDI carrier plates are the same shape and size as the microtiter plates and are able to accept the same number of samples as the microtiter plates according to the invention for the method according to the invention. The peptides are integrated into the cinnamic acid crystals used as the MALDI matrix and which form during the drying process. The dried carrier plate is now ready for recording the MALDI Time-Of-Flight mass spectrum for the peptides. From their precise masses, it is now possible to look for the protein in a protein sequence database in the usual way.

A proteome containing approx. 4,600 proteins can therefore be punched out automatically within about eight hours, processed in twelve 384 microtiter plates, four plates at a time, and incubated together for the digestion and then centrifuged together. The peptides on the MALDI plates can be measured in the mass spectrometer automatically. This takes about 12 hours using the technology which is currently available. Using automated mass spectrometers, the peptides of a complete proteome can be measured in a single night. The proteins are identified in real time while the spectrum is being recorded for the next sample.

Proteins which, as described in the introduction, contain peptides with lengths different to those in the protein sequence database can then be determined by their sequence or their deviations by recording the Post-Source-Decay (PSD) daughter-ion spectra of the individual peptides. Using the technology according to the invention, losses due to wall-adsorbed peptides practically never occur.

This method using the processes according to the invention has the following advantages when used in the devices according to the invention:

(1) The method is quick: the analysis of a proteome using a simple method for identifying the proteins can be carried out within approx. two to three days and the situation is avoided where sensitive proteins, which are only stable in their natural environment in the cell, decompose and cannot be analyzed. The extensive elucidation of structural differences which requires elaborate interactive operations is generally not included.

(2) The analysis is very simple: work is still in progress on automation.

(3) The detection rate for the individual peptides or a protein is high: in comparison with the usual processing-in-vessels procedures used so far, the detection rate of peptides is considerable higher. In particular, it was the strongly hydrophobic peptides which were often lost due to the effect of the walls when applying previously used technology and they were not detected in the mass-spectrometric measurement. As proteome research increasingly focuses its view on the deviations between real proteins and the sequences in the protein databases, these peptide losses are no longer acceptable.

Knowing about this invention and its application will enable every technician specialising in the field of biochemical microprocessing to meet his particular needs during his processing procedures by applying the basic principles outlined here, even if the special nature of the processing procedure has not been described here. For example, he will easily be able to adapt the method to different types of analysis using mass spectrometry.

So, for example, it is easily possible to transfer the eluted peptides to a micro-column liquid chromatograph where the separated peptides are then ionized via a nanoelectro-spray device and then measured using a ion trap mass spectrometer.

What is claimed is:

1. A method for the sample preparation of proteins contained in gel pieces for mass spectrometric analysis using enzymatic digestion of the proteins to peptides in the gel, the method comprising:
   locating the gel pieces containing the proteins in vessels having lyophobic porous bottoms;
   adding enzyme solution that is absorbed by each of the gel pieces such that the proteins are digested within the gel pieces to produce peptides; and
   removing enzyme solution and peptides from the gel pieces by centrifuging.

2. The method according to claim 1, wherein the peptides produced by digestion are adsorbed onto surfaces of the vessels.

3. The method according to claim 1, wherein the enzyme solution and peptides are directed from the vessels to at least one MALDI sample-carrier plate.

4. The method according to claim 3, wherein the peptides are adsorbed reversibly onto coatings on the sample-carrier plate and are subsequently subjected to a cleaning process.

5. The method according to claim 1, wherein the enzyme solution and peptides are collected, during centrifuging, in collection vessels.

6. The method according to claim 5, wherein the peptides are reversibly adsorbed onto surfaces of particles located in the collection vessels and are subsequently subjected to a cleaning process while on the particles.

7. The method according to claim 6, wherein the particles have magnetic cores that allow the particles to be arrested or moved in magnetic fields.

8. The method according to claim 2, wherein the peptides form reversibly adsorptive or adhesive bonds on the porous structures of the vessel bottoms, and are subsequently cleaned by a washing process and eluted by an eluting process.

9. The method according to claim 8, wherein the washing process and the eluting process comprise centrifuging.

10. The method according to claim 1, further comprising at least partially drying the gel pieces before adding the enzyme solutions.

11. The method according to claim 10, wherein drying is carried out at least partially by evacuation.

12. A device for carrying out the method of claim 1, comprising a plate in which the vessels are located, each vessel having at least one capillary channel with a lyophobic internal surface in a bottom of the vessel, a size of the capillary and lyophobicity of the capillary internal surface being sufficient to prevent an escape of liquid contents from the vessel under a normal force of gravity.

13. A device according to claim 12, wherein the plate is such that the vessels are equally spaced apart in a grid, and wherein a relative separation between vessels is an integer factor of nine millimeters.

14. A device according to claim 12, wherein the bottoms of the vessels have narrow ribs or grooves adjacent to the capillary channels.

15. A device according to claim 12, wherein the capillary channels each have a porous seal comprising an under-pressed membrane which adsorbs peptides reversibly.

16. A device according to claim 12, wherein the capillary channels each have a porous seal comprising a particle packing.

17. A device according to claim 12, wherein each capillary channel is closed off with a surface-active, open pore solid foam.

18. A device according to claim 12, wherein an inner wall of each vessel above a capillary channel of the vessel is lyophobic.

* * * * *